United States Patent
Murakami et al.

(10) Patent No.: US 10,598,616 B2
(45) Date of Patent: Mar. 24, 2020

(54) X-RAY REFLECTOMETER

(71) Applicant: RIGAKU CORPORATION, Tokyo (JP)

(72) Inventors: Satoshi Murakami, Takatsuki (JP); Kazuhiko Omote, Tokyo (JP); Shinya Kikuta, Takatsuki (JP); Akihiro Ikeshita, Takatsuki (JP)

(73) Assignee: Rigaku Corporation, Akishima-shi, Tokyo (JP)

( * ) Notice: Subject to any disclaimer, the term of this patent is extended or adjusted under 35 U.S.C. 154(b) by 0 days.

(21) Appl. No.: 16/420,370

(22) Filed: May 23, 2019

(65) Prior Publication Data

US 2019/0277781 A1    Sep. 12, 2019

Related U.S. Application Data (63) Continuation of application No. PCT/JP2017/040880, filed on Nov. 14, 2017.

(30) Foreign Application Priority Data

Nov. 29, 2016 (JP) .............................. 2016-231401

(51) Int. Cl.
*G01N 23/20* (2018.01)
*G01N 23/20008* (2018.01)
*G01B 15/02* (2006.01)

(52) U.S. Cl.
CPC ....... *G01N 23/20008* (2013.01); *G01B 15/02* (2013.01); *G01N 23/20* (2013.01)

(58) Field of Classification Search
CPC ..... G01N 23/20008; G01N 2021/8822; G01N 2021/95676; G01N 21/33;
(Continued)

(56) References Cited

U.S. PATENT DOCUMENTS

| 5,949,847 A | 9/1999 | Terada et al. |
| 6,308,015 B1 | 10/2001 | Matsumoto |

(Continued)

FOREIGN PATENT DOCUMENTS

| CN | 1278610 A | 1/2001 |
| CN | 101017254 A | 8/2007 |

(Continued)

OTHER PUBLICATIONS

International Search Report of PCT/JP2017/040880 dated Feb. 13, 2018.
(Continued)

*Primary Examiner* — Irakli Kiknadze
(74) *Attorney, Agent, or Firm* — Sughrue Mion, PLLC (57) ABSTRACT

The X-ray reflectometer of the present invention includes: an irradiation angle variable unit (10) configured to vary an irradiation angle of a focused X-ray beam (6) with a sample surface (8*a*); a position sensitive detector (14) which is fixed; and a reflection intensity calculation unit (15) configured to, per reflection angle of reflected X-rays (13) constituting a reflected X-ray beam (12), integrate a detected intensity by a corresponding detection element (11), for only the detection elements (11) positioned within a divergence angle width of the reflected X-ray beam (12) in the position sensitive detector (14), in synchronization of variation in the irradiation angle (θ) of the focused X-ray beam (6) by the irradiation angle variable unit (10).

13 Claims, 2 Drawing Sheets

(58) Field of Classification Search
CPC ........... G01N 21/95623; G01N 23/207; G01N 23/20; G01N 23/20091; G01N 2223/6116; G01N 23/201; G01N 2223/0563; G01N 2223/501; G01N 2223/646; G01N 2223/6462; G01N 23/087; G01N 23/20025; G01N 23/2055; G01N 23/2076; G01N 23/04; G01N 15/1456; G01N 2015/1486; G01N 2015/1493; G01N 2223/056; G01N 2223/0566; G01N 2223/301; G01N 2223/33; G01N 2223/607; G01N 2223/615; G01N 2291/0421; G01N 2223/076; G01N 23/223; G01N 2223/32; G01N 23/20016; G01N 23/205; G01B 15/02
USPC .................................. 378/62, 70–85, 201
See application file for complete search history.

(56) References Cited

U.S. PATENT DOCUMENTS

| | | | |
|---|---|---|---|
| 6,947,520 B2 | 9/2005 | Yokhin et al. | |
| 7,062,013 B2 | 6/2006 | Berman et al. | |
| 7,113,566 B1 | 9/2006 | Peled et al. | |
| 7,130,376 B2 | 10/2006 | Berman et al. | |
| 7,221,734 B2 | 5/2007 | Omote | |
| 7,920,676 B2 * | 4/2011 | Yun .................... | G03F 7/70625 378/70 |
| 8,111,807 B2 * | 2/2012 | Ida ....................... | G01N 23/207 378/70 |
| 8,243,878 B2 * | 8/2012 | Yokhin ................ | G01N 23/207 378/70 |
| 8,437,450 B2 * | 5/2013 | Wall .................... | G01N 23/207 378/73 |
| 8,687,766 B2 * | 4/2014 | Wormington ........ | G01N 23/207 378/70 |
| 2004/0109531 A1 | 6/2004 | Yokhin et al. | |
| 2004/0131151 A1 | 7/2004 | Berman et al. | |
| 2005/0207532 A1 | 9/2005 | Omote | |
| 2006/0153333 A1 | 7/2006 | Berman et al. | |
| 2008/0095311 A1 * | 4/2008 | Zheng ................... | G01N 23/20 378/71 |
| 2013/0039460 A1 * | 2/2013 | Levy .................... | G01N 21/211 378/44 |
| 2013/0129052 A1 * | 5/2013 | Toraya ................. | G01N 23/207 378/71 |
| 2014/0270079 A1 * | 9/2014 | Pedersen .............. | G01N 23/201 378/71 |
| 2014/0291518 A1 * | 10/2014 | Soejima ............... | G01N 23/223 250/310 |

FOREIGN PATENT DOCUMENTS

| | | |
|---|---|---|
| CN | 102589452 A | 7/2012 |
| CN | 205363813 U | 7/2016 |
| JP | 10-185846 A | 7/1998 |
| JP | 2002-365242 A | 12/2002 |
| JP | 2003-202306 A | 7/2003 |
| JP | 2004-191376 A | 7/2004 |
| JP | 2005-265742 A | 9/2005 |
| JP | 2007-024894 A | 2/2007 |
| JP | 2010-256259 A | 11/2010 |

OTHER PUBLICATIONS

Communication dated Oct. 30, 2019, from the State Intellectual Property Office of the P.R. of China in counterpart Application No. 201780073230.2.

* cited by examiner

X-RAY REFLECTOMETER

CROSS REFERENCE TO THE RELATED APPLICATION

This application is a continuation application, under 35 U.S.C. § 111(a), of international application No. PCT/JP2017/040880, filed Nov. 14, 2017, which claims priority to Japanese patent application No. 2016-231401, filed Nov. 29, 2016, the entire disclosure of which is herein incorporated by reference as a part of this application.

BACKGROUND OF THE INVENTION

Field of the Invention

The present invention relates to an X-ray reflectometer.

Description of Related Art

Conventionally, in X-ray reflectivity measurement, a sample such as a thin film is irradiated with an X-ray beam, a reflectivity curve which is the relationship between the reflection angle and the X-ray reflectivity of the reflected X-rays is obtained, and the film thickness, the surface roughness, the density, and the like of the sample are analyzed on the basis of the reflectivity curve. For example, there is known an X-ray reflectometer that rotates a reflected X-ray detection unit in synchronization with rotation of an X-ray source for a parallel X-ray beam, using a goniometer, for obtaining the reflectivity curve (Patent Document 1, FIG. 1(B), etc.). In this X-ray reflectometer, since the X-ray source and the detection unit are synchronously rotated in a necessary reflection angle range, the structure thereof is complicated and a certain time period is required for measurement. In addition, since a parallel X-ray beam narrowed into a needle shape or a band shape is applied, the intensity of the reflected X-ray is insufficient depending on the sample, and a further long time period is required for accurate analysis.

On the other hand, there is known an X-ray reflectometer in which, for obtaining the reflectivity curve, a focused X-ray beam is applied from a fixed X-ray source to a sample, and reflected by the sample so as to diverge as a reflected X-ray beam, and the intensities of the reflected X-rays constituting the reflected X-ray beam and having different reflection angles are detected by detection elements corresponding to the respective reflection angles in a fixed position sensitive detector (Patent Document 2, FIG. 1, etc.). In this X-ray reflectometer, since the X-ray source and the position sensitive detector are both fixed, the structure thereof is simple and measurement can be performed in a short time. In addition, since a focused X-ray beam is applied, the intensities of the reflected X-rays are less likely to be insufficient.

RELATED DOCUMENT

Patent Document

[Patent Document 1] JP Laid-open Patent Publication No. 2005-265742

[Patent Document 2] JP Laid-open Patent Publication No. 2004-191376

SUMMARY OF THE INVENTION

However, in the X-ray reflectometer described in Patent Document 2, a reflectivity curve can be obtained only in the range (width) of the focusing angle of the focused X-ray beam, i.e., the divergence angle of the reflected X-ray beam. Therefore, depending on the sample, a reflectivity curve in a sufficient reflection angle range cannot be obtained and thus it might be impossible to perform accurate analysis. On the other hand, if the focusing angle of the focused X-ray beam is set to be excessively great in order to broaden the reflection angle range, background due to scattered X-rays increases and a reflectivity curve with a high dynamic range cannot be obtained. Therefore, it might be impossible to perform accurate analysis after all.

Accordingly, the present invention has been made in view of the above conventional problems, and an object of the present invention is to provide an X-ray reflectometer which has a comparatively simple structure and which obtains reflected X-rays having sufficient intensities in a sufficient reflection angle range within a short time and sufficiently reduces background due to scattered X-rays, thereby enabling accurate analysis.

In order to attain the above object, an X-ray reflectometer according to the present invention includes: a focused X-ray beam formation unit having an X-ray source which emits X-rays, a focusing device which focuses the X-rays from the X-ray source, and a slit which limits a focusing angle width of the X-rays focused by the focusing device, to form a focused X-ray beam; a sample height setting unit having a sample table allowing a sample to be placed thereon, and configured to move the sample table in a height direction to set a height of a sample surface thereof; and an irradiation angle variable unit configured to vary an irradiation angle of the focused X-ray beam with the sample surface.

The X-ray reflectometer according to the present invention further includes: a position sensitive detector having a plurality of detection elements arranged in the height direction and configured to, for a reflected X-ray beam obtained by the focused X-ray beam being reflected by the sample, detect each intensity of reflected X-rays constituting the reflected X-ray beam and having each individual reflection angle, by corresponding each detection element; and a reflection intensity calculation unit configured to, per reflection angle of the reflected X-rays constituting the reflected X-ray beam, integrate the detected intensity by the corresponding detection element, for only the detection elements positioned within a divergence angle width of the reflected X-ray beam in the position sensitive detector, in synchronization of variation in the irradiation angle of the focused X-ray beam by the irradiation angle variable unit.

In the X-ray reflectometer according to the present invention, the irradiation angle of the X-ray beam is varied, but it is sufficient that, using the focused X-ray beam having the focusing angle width and the fixed position sensitive detector, the irradiation angle of the focused X-ray beam is varied by an amount by which the focusing angle width is insufficient for the required reflection angle range. Therefore, with a comparatively simple structure, it is possible to obtain reflected X-rays having sufficient intensities in a sufficient reflection angle range within a short time. Then, for only the detection elements positioned within the divergence angle width of the reflected X-ray beam in the position sensitive detector, per reflection angle of the reflected X-rays constituting the reflected X-ray beam, the detected intensity by the corresponding detection element is integrated. Thus, it is possible to perform accurate analysis while sufficiently decreasing background due to scattered X-rays.

In the X-ray reflectometer according to the present invention, preferably, the irradiation angle variable unit rotates the focused X-ray beam formation unit about an axis on the sample surface, thereby varying the irradiation angle of the focused X-ray beam with the sample surface. In this case, when the irradiation angle of the focused X-ray beam is varied by the irradiation angle variable unit, the correspondence relationship between each reflection angle of the reflected X-rays constituting the reflected X-ray beam and the detection element detecting the intensity of the reflected X-ray having that reflection angle, does not vary.

In the X-ray reflectometer according to the present invention, it is preferable that: on the basis of a receiving distance from an irradiation position of the focused X-ray beam on the sample surface to a receiving surface of the position sensitive detector, the individual reflection angles of the reflected X-rays constituting the reflected X-ray beam and positions in the height direction of the detection elements to detect the intensities of the respective reflected X-rays, are associated with each other by triangulation; the X-ray reflectometer further comprises a calibration unit configured to calibrate the receiving distance; and for a critical angle reference sample with a known total reflection critical angle, the calibration unit calculates a position in the height direction of the detection element, corresponding to the total reflection critical angle, on the basis of a relationship between the reflection angles of the reflected X-rays constituting the reflected X-ray beam and the integrated detected intensities for the corresponding detection elements calculated by the reflection intensity calculation unit, and calculates a calibrated receiving distance by triangulation on the basis of the calculated position in the height direction and the known total reflection critical angle. In this case, the receiving distance is appropriately calibrated, whereby more accurate analysis can be performed.

In the X-ray reflectometer according to the present invention, it is also preferable that, for a film thickness value reference sample of which a film thickness value of a thin film formed on a surface thereof is known, the calibration unit calculates an oscillation period length, corresponding to the film thickness value, in the height direction of the detection elements on the basis of a relationship between the reflection angles of the reflected X-rays constituting the reflected X-ray beam and the integrated detected intensities for the corresponding detection elements calculated by the reflection intensity calculation unit, calculates, on the basis of the known film thickness value, a corresponding oscillation period angle in a reflection angle direction, and calculates a calibrated receiving distance by triangulation on the basis of the calculated oscillation period length in the height direction and the calculated oscillation period angle in the reflection angle direction. Also in this case, the receiving distance is appropriately calibrated, whereby more accurate analysis can be performed.

In the X-ray reflectometer according to the present invention, preferably, the slit for forming the focused X-ray beam is a variable slit configured to further limit the focusing angle width to form a nearly parallel X-ray beam, and the X-ray reflectometer further includes a half intensity height adjustment unit configured to adjust the height of the sample surface to a half intensity height by the sample height setting unit. Here, first, on the basis of a half intensity adjustment method, the half intensity height adjustment unit, in a state in which the sample is retracted by the sample height setting unit, causes the nearly parallel X-ray beam formed by the variable slit to be emitted toward the position sensitive detector, and stores, as a start intensity of half intensity adjustment, a detected intensity by the detection element that detects an intensity of the nearly parallel X-ray beam. Then, the half intensity height adjustment unit, while operating the sample height setting unit and the irradiation angle variable unit, monitors a detected intensity by the detection element that detects an intensity of the nearly parallel X-ray beam reflected by the sample, and adjusts to, as the half intensity height, a height of the sample surface in a state in which the detected intensity being monitored becomes half of the start intensity of half intensity adjustment and the detected intensity being monitored decreases if an irradiation angle of the nearly parallel X-ray beam is increased/decreased by the irradiation angle variable unit.

In this case, in spite of the X-ray reflectometer in a focusing optical system for which it is originally difficult to apply the half intensity adjustment method, it is possible to apply the half intensity adjustment method by forming the nearly parallel X-ray beam, and therefore the half intensity height can be appropriately set. Here, a position sensor configured to detect the height of the sample surface may be provided, and the half intensity height adjustment unit may store a half intensity height adjusted for a predetermined sample, by detecting the half intensity height using the position sensor, and adjust, for a given sample, a height of a sample surface thereof to the stored half intensity height by the sample height setting unit. In this case, it is not necessary to apply the half intensity adjustment method for each new sample, and thus a further preferable configuration is obtained.

Preferably, the X-ray reflectometer according to the present invention further includes a reflection angle correcting unit configured to correct a reflection angle associated with a position in the height direction of each detection element. Here, the reflection angle correcting unit, first, has stored, as an origin height position, a position in the height direction of the detection element that detects an intensity of the nearly parallel X-ray beam when the nearly parallel X-ray beam formed by the variable slit is emitted toward the position sensitive detector in a state in which the irradiation angle by the irradiation angle variable unit is set at 0 degrees and the sample is retracted by the sample height setting unit. Then, the reflection angle correcting unit stores, as a set angle corresponding height position, a position in the height direction of the detection element that detects an intensity of the nearly parallel X-ray beam formed by the variable slit and reflected by the sample, in a state in which the irradiation angle by the irradiation angle variable unit is a set angle smaller than a total reflection critical angle, and under the adjustment of the half intensity height by the half intensity height adjustment unit.

Further, for the integration of the detected intensity by the corresponding detection element per reflection angle by the reflection intensity calculation unit, the reflection angle correcting unit calculates the corrected reflection angle by triangulation on the basis of the origin height position, the receiving distance, the set angle, and the set angle corresponding height position. In this case, it is possible to correct the reflection angle immediately and appropriately even if the sample surface has been slightly inclined after the adjustment of the half intensity height by the half intensity height adjustment unit. Therefore, more accurate analysis can be performed immediately. In particular, in the aforementioned preferable configuration in which the half intensity height adjustment unit stores the half intensity height adjusted for the predetermined sample by detecting the half intensity height using the position sensor, and adjusts, for the given sample, the height of the sample surface thereof to the stored half intensity height, it is possible to correct the reflection angle more immediately and appropriately with respect to the inclination of the sample surface without applying the half intensity adjustment method for each new sample. Thus, more accurate analysis can be performed more immediately.

In the X-ray reflectometer according to the present invention, preferably, the position sensitive detector includes an attenuator configured to attenuate the intensity of the reflected X-ray beam at a part of a receiving surface thereof. In this case, saturation of the detected intensities at the detection elements corresponding to reflection angles in a total reflection region can be prevented, so that more accurate analysis can be performed. It is also preferable that the focused X-ray beam formation unit further has a knife edge slit located close to an irradiation position of the focused X-ray beam on the sample surface. In this case, X-rays emitted from the focused X-ray beam formation unit and going toward the position sensitive detector directly or while being scattered by air are shielded and background is decreased, whereby more accurate analysis can be performed.

In the X-ray reflectometer according to the present invention, preferably, when, for only the detection elements positioned within the divergence angle width of the reflected X-ray beam in the position sensitive detector, per reflection angle of the reflected X-rays constituting the reflected X-ray beam, integrating the detected intensity by the corresponding detection element, the reflection intensity calculation unit calculates a background intensity on the basis of the detected intensities by the detection elements positioned outside the divergence angle width of the reflected X-ray beam in the position sensitive detector, and subtracts the background intensity. In this case, using the detected intensities by the detection elements positioned outside the divergence angle width of the reflected X-ray beam, which are not integration targets though being detected, background intensities are calculated for the detected intensities by the detection elements that are integration targets, and the calculated background intensities are subtracted. Therefore, it is not necessary to perform separate measurement for calculating the background intensities, background can be further decreased immediately, and more accurate analysis can be performed.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
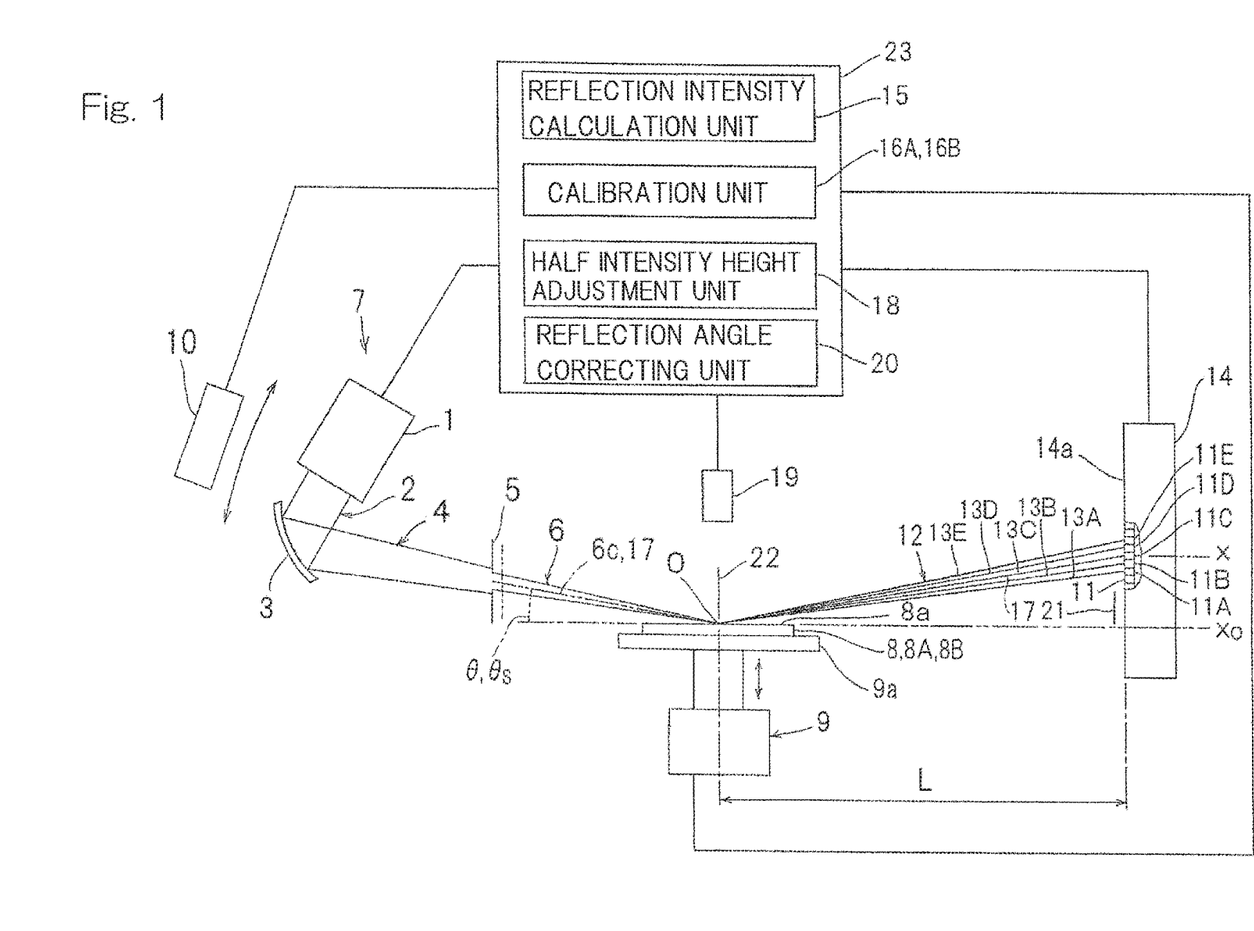
FIG. 1 is a schematic diagram of an X-ray reflectometer according to one embodiment of the present invention.

Hereinafter, an X-ray reflectometer according to one embodiment of the present invention will be described with reference to the drawings. As shown in FIG. 1, this X-ray reflectometer includes a focused X-ray beam formation unit 7 having: an X-ray source 1 which is an X-ray tube for emitting X-rays 2; a focusing device 3 which is a spectroscopic mirror for focusing the X-rays 2 from the X-ray source 1; and a slit 5 which limits a focusing angle width of X-rays 4 focused by the focusing device 3, to about one degree, thereby forming a focused X-ray beam 6. Here, the slit 5 is a variable slit 5 capable of further limiting the focusing angle width by a slit width becoming about 30 μm, thereby forming a nearly parallel X-ray beam 17 having a focusing angle of 1 mrad or less, or preferably, 0.5 mrad or less. The focused X-ray beam formation unit 7 further has a knife edge slit 22 located close to an irradiation position (where the applied focused X-ray beam becomes a line shape perpendicular to the drawing sheet of FIG. 1) of the focused X-ray beam 6 on a sample surface 8a. By the knife edge slit 22, X-rays emitted from the focused X-ray beam formation unit 7 and going toward the later-described position sensitive detector 14 directly or while being scattered by air are shielded and background is decreased, whereby more accurate analysis can be performed.

The X-ray reflectometer of the present embodiment further includes: a sample height setting unit 9 which has a sample table 9a allowing a sample 8 to be placed thereon and which moves the sample table 9a in a height direction to set a height of a sample surface 8a; and an irradiation angle variable unit 10 which varies an irradiation angle θ of the focused X-ray beam 6 with the sample surface 8a by about several degrees. Here, the irradiation angle θ of the focused X-ray beam 6 can be represented by, for example, an incident angle θ of central incident X-rays 6c among incident X-rays constituting the focused X-ray beam 6 and incident on the sample surface 8a at individual incident angles. In the X-ray reflectometer of the present embodiment, the irradiation angle variable unit 10 rotates the focused X-ray beam formation unit 7 about an axis O on the sample surface 8a, thereby varying the irradiation angle θ of the focused X-ray beam 6 with the sample surface 8a.

The X-ray reflectometer of the present embodiment further includes a position sensitive detector 14 which has a plurality of detection elements 11 arranged in the height direction and which, for a reflected X-ray beam 12 obtained by the focused X-ray beam 6 being reflected by the sample 8, detects each intensity of reflected X-rays 13 constituting the reflected X-ray beam 12 and having each individual reflection angle, by the corresponding each detection element 11. A width in the height direction of each detection element 11 is, for example, 75 μm. In FIG. 1, a partial cutaway view of the position sensitive detector 14 is shown, and for example, different detection elements 11A, 11B, 11C, 11D, 11E respectively correspond to reflected X-rays 13A, 13B, 13C, 13D, 13E having different reflection angles. It is noted that, in FIG. 1, for the purpose of facilitating illustration and understanding, the irradiation angle θ of the focused X-ray beam 6 (which also corresponds to a central reflection angle of the reflected X-ray beam 12), the focusing angle of the focused X-ray beam 6 (which also corresponds to a divergence angle of the reflected X-ray beam 12), an arrangement pitch of the detection elements 11, and the like are all shown in an exaggerated manner.

The position sensitive detector 14 may be a one-dimensional detector having the plurality of detection elements 11 arranged straightly in the height direction, or may be a two-dimensional detector having a plurality of detection elements arranged in a plane including the height direction and perpendicular to the drawing sheet of FIG. 1. In the X-ray reflectometer of the present embodiment, the one-dimensional detector is used. The position sensitive detector 14 has an attenuator 21 for attenuating the intensity of the reflected X-ray beam 12 at a part of a receiving surface 14a. By providing the attenuator 21, saturation of the detected intensities at the detection elements 11 corresponding to reflection angles in a total reflection region can be prevented, so that more accurate analysis can be performed.

The X-ray reflectometer of the present embodiment further includes a reflection intensity calculation unit 15 which, per reflection angle of the reflected X-rays 13 (in FIG. 1, 13A to 13E) constituting the reflected X-ray beam 12, integrates the detected intensity by the corresponding detection element 11 (in FIG. 1, 11A to 11E), for only the detection elements 11 (in FIG. 1, 11A to 11E) positioned within the divergence angle width of the reflected X-ray beam 12 in the position sensitive detector 14, in synchronization of variation in the irradiation angle θ of the focused X-ray beam 6 by the irradiation angle variable unit 10. The reflection intensity calculation unit 15 is included, together with a calibration unit 16A, a half intensity height adjustment unit 18, and a reflection angle correcting unit 20 described later, in a control unit 23, e.g., a computer, which controls the X-ray reflectometer.

Here, according to the irradiation angle variable unit 10 included in the X-ray reflectometer of the present embodiment, when the irradiation angle θ of the focused X-ray beam 6 varies, the correspondence relationship between each reflection angle of the reflected X-rays 13 constituting the reflected X-ray beam 12 and the detection element 11 detecting the intensity of the reflected X-ray 13 having that reflection angle, does not vary. For example, the detection element 11C corresponds to the reflection angle of the reflected X-ray 13C in FIG. 1, and the corresponding relationship therebetween does not vary even if the irradiation angle θ of the focused X-ray beam 6 varies.

Instead of the irradiation angle variable unit 10, an irradiation angle variable unit may be provided which rotates the sample table 9a about the axis O on the sample surface 8a, thereby varying the irradiation angle θ of the focused X-ray beam 6 with the sample surface 8a. In this case, if the irradiation angle θ of the focused X-ray beam 6 increases by α, the detection element 11 corresponding to a certain reflection angle changes to another detection element 11 located at a position higher by a height corresponding to α. Therefore, in integration of the detected intensity for each reflection angle, the detected intensities are integrated while the detection element 11 corresponding to each reflection angle is being tracked in synchronization with variation in the irradiation angle θ of the focused X-ray beam 6.

In the X-ray reflectometer of the present embodiment, the irradiation angle θ of the focused X-ray beam 6 is varied, but it is sufficient that, using the focused X-ray beam 6 having a focusing angle width and the fixed position sensitive detector 14, the irradiation angle of the focused X-ray beam 6 is varied by an amount by which the focusing angle width is insufficient for the required reflection angle range. Therefore, with a comparatively simple structure, it is possible to obtain reflected X-rays 13 having sufficient intensities in a sufficient reflection angle range within a short time. Then, for only the detection elements 11 positioned within the divergence angle width of the reflected X-ray beam 12 in the position sensitive detector 14, per reflection angle of the reflected X-rays 13 constituting the reflected X-ray beam 12, the detected intensity by the corresponding detection element 11 is integrated and the detected intensities by the detection elements 11 positioned outside the divergence angle width of the reflected X-ray beam 12 are excluded. Thus, it is possible to perform accurate analysis while sufficiently decreasing background due to scattered X-rays.

Further, in the X-ray reflectometer of the present embodiment, on the basis of a receiving distance L from the irradiation position (indicated by the same O as the axis on the sample surface 8a described above) of the focused X-ray beam 6 on the sample surface 8a to the receiving surface 14a of the position sensitive detector 14, the individual reflection angles of the reflected X-rays 13 constituting the reflected X-ray beam 12 and positions in the height direction of the detection elements 11 to detect the intensities of the respective reflected X-rays 13 are associated with each other by triangulation, and the calibration unit 16A for calibrating the receiving distance L is provided. For a critical angle reference sample 8A with a known total reflection critical angle $\theta_C$, the calibration unit 16A calculates a position $x_C$ in the height direction of the detection element 11, corresponding to the total reflection critical angle $\theta_C$, on the basis of a relationship between the reflection angles of the reflected X-rays 13 constituting the reflected X-ray beam 12 and the integrated detected intensities for the corresponding detection elements 11 calculated by the reflection intensity calculation unit 15, and calculates a calibrated receiving distance L by triangulation on the basis of the calculated position $x_C$ in the height direction and the known total reflection critical angle $\theta_C$.

Specifically, the relationship between the reflection angles and the integrated detected intensities for the corresponding detection elements 11 corresponds to a so-called reflectivity curve. Therefore, the reflection angle at an inflection point where the integrated detected intensity sharply decreases relative to increase in the reflection angle corresponds to the total reflection critical angle $\theta_C$, and the position $x_C$ in the height direction of the detection element 11, corresponding to the total reflection critical angle $\theta_C$, i.e., the reflection angle at the inflection point is calculated. Then, the calibrated receiving distance L is calculated from the following formula (1). Thus, the receiving distance L is appropriately calibrated by the calibration unit 16A, whereby more accurate analysis can be performed.

$$L = x_C / \tan \theta_C \qquad (1)$$

Instead of the above calibration unit 16A, a calibration unit 16B shown below may be provided. For a film thickness value reference sample 8B of which the film thickness value of a thin film formed on a surface thereof is known, the calibration unit 16B calculates an oscillation period length Δx, corresponding to the film thickness value, in the height direction of the detection element 11 on the basis of the relationship between the reflection angles of the reflected X-rays 13 constituting the reflected X-ray beam 12 and the integrated detected intensities for the corresponding detection elements 11 calculated by the reflection intensity calculation unit 15, on the basis of the known film thickness value, a corresponding oscillation period angle Δθ in a reflection angle direction, and then calculates a calibrated receiving distance L by triangulation on the basis of the calculated oscillation period length Δx in the height direction and the calculated oscillation period angle Δθ in the reflection angle direction.

Specifically, the relationship between the reflection angles and the integrated detected intensities for the corresponding detection elements 11 corresponds to a so-called reflectivity curve as described above. Therefore, the oscillation period angle with which the integrated detected intensity increases/decreases relative to increase in the reflection angle corresponds to the film thickness value, and the oscillation period length Δx, corresponding to the oscillation period angle, in the height direction of the detection element 11 is calculated. Meanwhile, from a reflectivity curve theoretically calculated on the basis of the known film thickness value, the oscillation period angle Δθ, corresponding to the film thickness value, in the reflection angle direction is calculated, and the calibrated receiving distance L is calculated from the following formula (2). Thus, even by the calibration unit 16B, the receiving distance L can be appropriately calibrated, whereby more accurate analysis can be performed.

$$L = \Delta x / \tan \Delta\theta \quad (2)$$

The X-ray reflectometer of the present embodiment further includes the half intensity height adjustment unit 18 which adjusts the height of the sample surface 8a to a half intensity height by the sample height setting unit 9. On the basis of a half intensity adjustment method, first, the half intensity height adjustment unit 18, in a state in which the sample 8 is retracted by the sample height setting unit 9, causes the nearly parallel X-ray beam 17 formed by the variable slit 5 described above to be emitted toward the position sensitive detector 14, and stores a detected intensity by the detection element 11 that detects an intensity of the nearly parallel X-ray beam 17, as a start intensity of half intensity adjustment. Then, the half intensity height adjustment unit 18, while operating the sample height setting unit 9 and the irradiation angle variable unit 10, monitors a detected intensity by the detection element 11 that detects an intensity of the nearly parallel X-ray beam 17 reflected by the sample 8, and adjusts to, as the half intensity height, a height of the sample surface 8a in a state in which the detected intensity being monitored becomes half of the start intensity of half intensity adjustment and the detected intensity being monitored decreases if the irradiation angle θ of the nearly parallel X-ray beam 17 is increased/decreased by the irradiation angle variable unit 10.

Thus, in spite of the X-ray reflectometer in a focusing optical system for which it is originally difficult to apply the half intensity adjustment method, it is possible to apply the half intensity adjustment method by forming the nearly parallel X-ray beam 17, and therefore the half intensity height can be appropriately set. Here, the X-ray reflectometer of the present embodiment includes a position sensor 19 for detecting the height of the sample surface 8a, and the half intensity height adjustment unit 18 stores a half intensity height adjusted for a predetermined sample 8, by detecting the half intensity height using the position sensor 19, and adjusts, for a given sample 8, a height of a sample surface 8a thereof to the stored half intensity height by the sample height setting unit 9. Therefore, it is not necessary to apply the half intensity adjustment method for each new sample 8.

The X-ray reflectometer of the present embodiment further includes the reflection angle correcting unit 20 which corrects a reflection angle associated with a position in the height direction of each detection element 11. First, the reflection angle correcting unit 20 has stored, as an origin height position $x_O$, a position in the height direction of the detection element 11 that detects an intensity of the nearly parallel X-ray beam 17 when the nearly parallel X-ray beam 17 formed by the variable slit 5 is emitted toward the position sensitive detector 14 in a state in which the irradiation angle by the irradiation angle variable unit 10 is set at 0 degrees and the sample 8 is retracted by the sample height setting unit 9. Then, in a state in which the irradiation angle by the irradiation angle variable unit 10 is a set angle $\theta_S$ which is smaller than a total reflection critical angle so that the detected intensity can be stably obtained, and under the adjustment of the half intensity height by the half intensity height adjustment unit 18, the reflection angle correcting unit 20 stores, as a set angle corresponding height position x, a position in the height direction of the detection element 11 that detects an intensity of the nearly parallel X-ray beam 17 formed by the variable slit 5 and reflected by the sample 8. Further, for integration of the detected intensity by the corresponding detection element 11 per reflection angle by the reflection intensity calculation unit 15, the reflection angle correcting unit 20 calculates the corrected reflection angle by triangulation on the basis of the origin height position $x_O$, the receiving distance L, the set angle $\theta_S$, and the set angle corresponding height position x.

Specifically, after the half intensity height is adjusted by the half intensity height adjustment unit 18, it is assumed that a sample surface 8a of an analytical sample 8 which should be horizontal is inclined by δ in a direction in which the irradiation angle θ decreases (clockwise direction in FIG. 1), for example. In this case, when the irradiation angle of the nearly parallel X-ray beam 17 is the set angle $\theta_S$ smaller than the total reflection critical angle, the true irradiation angle θ is $\theta_S - \delta$. When the irradiation angle of the nearly parallel X-ray beam 17 is set at $\theta_S$, if the set angle corresponding height position in the case where the sample surface 8a is horizontal is denoted by $x_S$, the inclination δ of the sample surface 8a when the set angle corresponding height position becomes x is represented by the following formula (3). If the origin height position $x_O$ is set as 0 and $x_S = L \tan \theta_S$ is substituted, the following formula (4) is obtained.

$$\delta = \tan^{-1}((x_S - x)/2L) \quad (3)$$

$$\delta = \tan^{-1}((L \tan \theta_S - x)/2L) \quad (4)$$

A relationship between the set angle $\theta_S$ and the true irradiation angle θ also corresponds to a relationship between the reflection angle before correction and the corrected reflection angle. Therefore, if the inclination δ of the sample surface 8a represented by formula (4) is subtracted from the reflection angle in the case where the sample surface 8a is horizontal, the corrected reflection angle is calculated.

Thus, by the reflection angle correcting unit 20, it is possible to correct the reflection angle immediately and appropriately even if the sample surface 8a has been slightly inclined after the adjustment of the half intensity height by the half intensity height adjustment unit 18. Therefore, more accurate analysis can be performed immediately. In particular, in the X-ray reflectometer of the present embodiment, the half intensity height adjustment unit 18 stores the half intensity height adjusted for the predetermined sample 8 by detecting the half intensity height using the position sensor 19, and can adjust, for the given sample 8, the height of the sample surface 8a thereof to the stored half intensity height. Therefore, it is possible to correct the reflection angle more immediately and appropriately with respect to the inclination δ of the sample surface 8a without applying the half intensity adjustment method for each new sample 8. Thus, more accurate analysis can be performed more immediately.

It is noted that the incident angle of the incident X-rays included in the focused X-ray beam 6 and incident on the sample surface 8a is identical to the reflection angle of the reflected X-rays 13 obtained by the incident X-rays being reflected, and the detection elements 11 are associated with the respective reflection angles on the basis of a geometric relationship. Therefore, correcting each reflection angle of the reflected X-rays 13 constituting the reflected X-ray beam 12 with respect to the inclination δ of the sample surface 8a is equivalent to and has the same meaning as correcting the position, corresponding to each reflection angle, in the height direction of the detection element 11 or correcting the irradiation angle θ.

Further, in the X-ray reflectometer of the present embodiment, when, for only the detection elements 11 (in FIG. 1, 11A to 11E) positioned within the divergence angle width of the reflected X-ray beam 12 in the position sensitive detector 14, per reflection angle of the reflected X-rays 13 (in FIG. 1, 13A to 13E) constituting the reflected X-ray beam 12, integrating the detected intensity by the corresponding detection element 11 (in FIG. 1, 11A to 11E), the reflection intensity calculation unit 15 calculates a background intensity on the basis of the detected intensities by the detection elements 11 positioned outside the divergence angle width of the reflected X-ray beam 12 in the position sensitive detector, and subtracts the background intensity.

Figure 2:
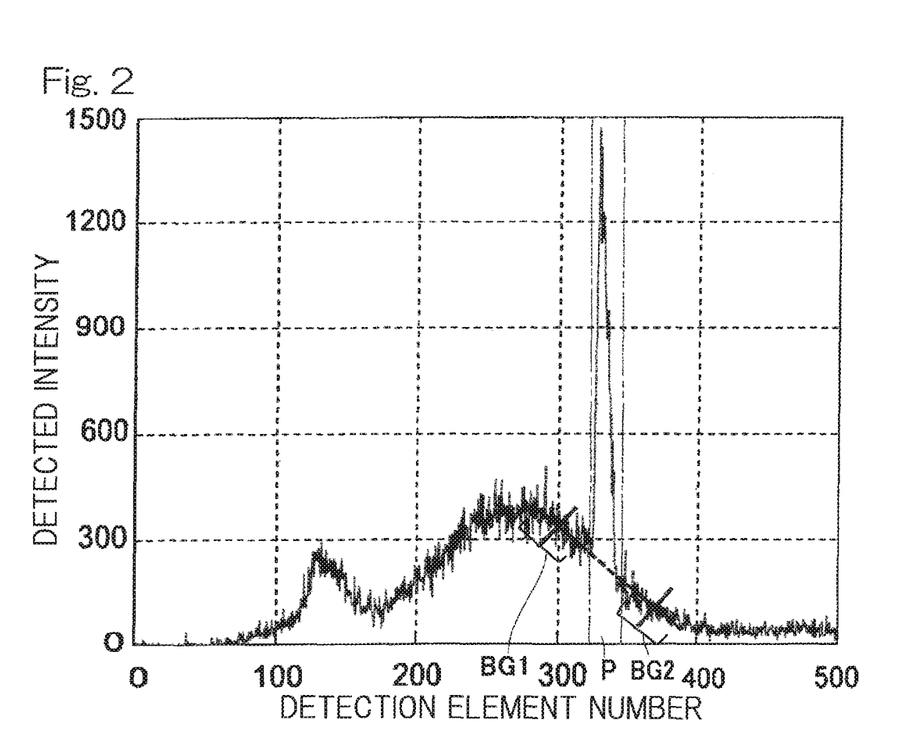
FIG. 2 shows background correction by the X-ray reflectometer.

A specific example of the above background correction will be described with reference to FIG. 2. FIG. 2 shows the detected intensities by the detection elements 11 continuously, when the focused X-ray beam 6 is set at a certain irradiation angle. The abscissa axis indicates the numbers of the detection elements 11 and corresponds to the positions in the height direction of the detection elements 11. The ordinate axis indicates the detected intensities. The detection elements 11 in an area P (hereinafter, may be referred to as peak area) between two dashed two-dotted lines in the abscissa axis are positioned within the divergence angle width of the reflected X-ray beam 12.

First, near the left and right sides of the peak area P, background sampling areas BG1, BG2 (in FIG. 2, indicated by "[" which is not horizontal but descends rightward) separated by a predetermined distance and having a predetermined width in the abscissa axis direction are set. Then, the average value of detected intensities in each sampling area BG1, BG2 is calculated, and the calculated average value of the detected intensities is defined as a detected intensity at the center in the abscissa axis direction in each sampling area BG1, BG2 (hereinafter, may be referred to as representative detected intensity).

Further, a linear function (straight line indicated by broken line in FIG. 2) connecting the two points indicating the representative detected intensities in both sampling areas BG1, BG2 is calculated, and then, in the peak area P, the intensities on the calculated straight line are subtracted, as background intensities by the respective detection elements 11, from the detected intensities by the respective detection elements 11. It is noted that the subtraction of the background intensities may be performed for individual detected intensities, or similarly to the case of detected intensities, the background intensity may be integrated per reflection angle of the reflected X-rays 13 and the integrated background intensity may be subtracted from the integrated detected intensity. The setting of background sampling areas and the way to calculate the background intensities are not limited to the above examples, but various methods are applicable.

In this background correction, using the detected intensities by the detection elements 11 positioned outside the divergence angle width of the reflected X-ray beam 12 (in FIG. 2, outside the peak area P), which are not integration targets though being detected, background intensities are calculated for the detected intensities by the detection elements 11 that are integration targets (in FIG. 2, inside the peak area P), and the calculated background intensities are subtracted. Therefore, it is not necessary to perform separate measurement for calculating the background intensities, background can be further decreased immediately, and more accurate analysis can be performed.

Figure 3:
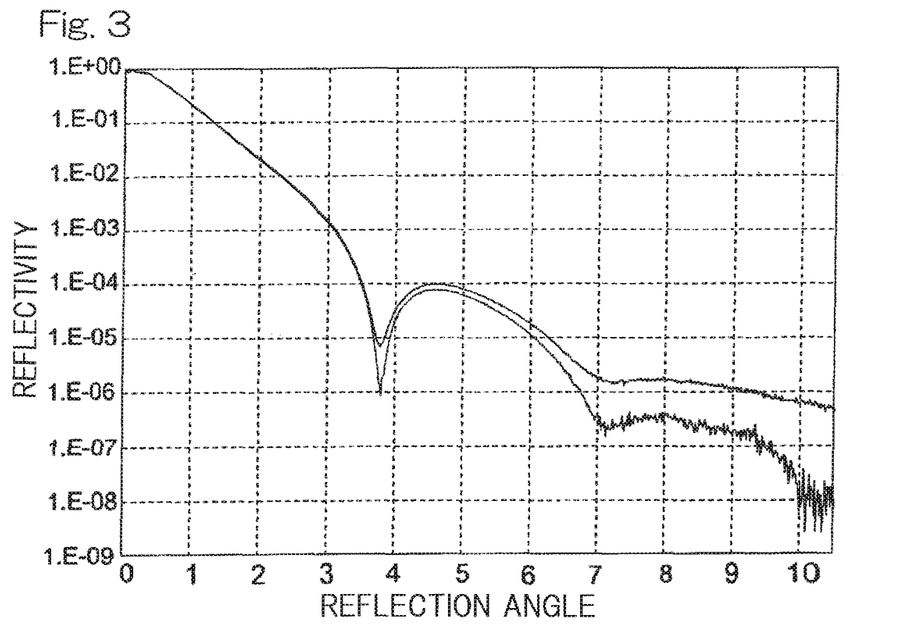
FIG. 3 shows a reflectivity curve obtained by the X-ray reflectometer according to the present invention.

FIG. 3 shows reflectivity curves obtained by the X-ray reflectometer of the present invention. The abscissa axis indicates the reflection angles of the reflected X-rays 13. Of the two reflectivity curves shown, the lower-side one has undergone the above background correction and the upper-side one has not undergone the background correction. In either case, it is understood that the reflectivity is obtained with a sufficiently high dynamic range over a sufficiently wide reflection angle range, and in particular, performing the above background correction enhances the dynamic range by about double digits.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . X-ray source
2 . . . X-rays from X-ray source
3 . . . focusing device
4 . . . X-rays focused by focusing device
5 . . . slit (variable slit)
6 . . . focused X-ray beam
7 . . . focused X-ray beam formation unit
8 . . . sample
8a . . . sample surface
8A . . . critical angle reference sample
8B . . . film thickness value reference sample
9 . . . sample height setting unit
9a . . . sample table
10 . . . irradiation angle variable unit
11 . . . detection element
12 . . . reflected X-ray beam
13 . . . reflected X-rays
14 . . . position sensitive detector
14a . . . receiving surface of position sensitive detector
15 . . . reflection intensity calculation unit
16A, 16B . . . calibration unit
17 . . . nearly parallel X-ray beam
18 . . . half intensity height adjustment unit
19 . . . position sensor
20 . . . reflection angle correcting unit
21 . . . attenuator
22 . . . knife edge slit
O . . . axis on sample surface (irradiation position of focused X-ray beam)
x . . . set angle corresponding height position $x_O$ . . . origin height position
θ . . . irradiation angle of focused X-ray beam
$θ_S$ . . . set angle

What is claimed is:

1. An X-ray reflectometer comprising:
    a focused X-ray beam formation unit having an X-ray source which emits X-rays, a focusing device which focuses the X-rays from the X-ray source, and a slit which limits a focusing angle width of the X-rays focused by the focusing device, to form a focused X-ray beam;
    a sample height setting unit having a sample table allowing a sample to be placed thereon, and configured to move the sample table in a height direction to set a height of a sample surface thereof;
    an irradiation angle variable unit configured to vary an irradiation angle of the focused X-ray beam with the sample surface;
    a position sensitive detector having a plurality of detection elements arranged in the height direction and configured to, for a reflected X-ray beam obtained by the focused X-ray beam being reflected by the sample, detect each intensity of reflected X-rays constituting the reflected X-ray beam and having each individual reflection angle, by corresponding each detection element; and
    a reflection intensity calculation unit configured to, per reflection angle of the reflected X-rays constituting the reflected X-ray beam, integrate the detected intensity by the corresponding detection element, for only the detection elements positioned within a divergence angle width of the reflected X-ray beam in the position sensitive detector, in synchronization of variation in the irradiation angle of the focused X-ray beam by the irradiation angle variable unit.

2. The X-ray reflectometer as claimed in claim 1, wherein the irradiation angle variable unit rotates the focused X-ray beam formation unit about an axis on the sample surface, thereby varying the irradiation angle of the focused X-ray beam with the sample surface.

3. The X-ray reflectometer as claimed in claim 1, wherein on the basis of a receiving distance from an irradiation position of the focused X-ray beam on the sample surface to a receiving surface of the position sensitive detector, the individual reflection angles of the reflected X-rays constituting the reflected X-ray beam and positions in the height direction of the detection elements to detect the intensities of the respective reflected X-rays, are associated with each other by triangulation,
the X-ray reflectometer further comprises a calibration unit configured to calibrate the receiving distance, and
for a critical angle reference sample with a known total reflection critical angle, the calibration unit calculates a position in the height direction of the detection element, corresponding to the total reflection critical angle, on the basis of a relationship between the reflection angles of the reflected X-rays constituting the reflected X-ray beam and the integrated detected intensities for the corresponding detection elements calculated by the reflection intensity calculation unit, and calculates a calibrated receiving distance by triangulation on the basis of the calculated position in the height direction and the known total reflection critical angle.

4. The X-ray reflectometer as claimed in claim 1, wherein on the basis of a receiving distance from an irradiation position of the focused X-ray beam on the sample surface to a receiving surface of the position sensitive detector, the individual reflection angles of the reflected X-rays constituting the reflected X-ray beam and positions in the height direction of the detection elements to detect the intensities of the respective reflected X-rays, are associated with each other by triangulation,
the X-ray reflectometer further comprises a calibration unit configured to calibrate the receiving distance, and
for a film thickness value reference sample of which a film thickness value of a thin film formed on a surface thereof is known, the calibration unit calculates an oscillation period length, corresponding to the film thickness value, in the height direction of the detection elements on the basis of a relationship between the reflection angles of the reflected X-rays constituting the reflected X-ray beam and the integrated detected intensities for the corresponding detection elements calculated by the reflection intensity calculation unit, calculates, on the basis of the known film thickness value, a corresponding oscillation period angle in a reflection angle direction, and calculates a calibrated receiving distance by triangulation on the basis of the calculated oscillation period length in the height direction and the calculated oscillation period angle in the reflection angle direction.

5. The X-ray reflectometer as claimed in claim 3, wherein the slit to form the focused X-ray beam is a variable slit configured to further limit the focusing angle width to form a nearly parallel X-ray beam,
the X-ray reflectometer further comprises a half intensity height adjustment unit configured to adjust the height of the sample surface to a half intensity height by the sample height setting unit, and
the half intensity height adjustment unit, on the basis of a half intensity adjustment method,
    in a state in which the sample is retracted by the sample height setting unit, causes the nearly parallel X-ray beam formed by the variable slit to be emitted toward the position sensitive detector, and stores, as a start intensity of half intensity adjustment, a detected intensity by the detection element that detects an intensity of the nearly parallel X-ray beam, and
    while operating the sample height setting unit and the irradiation angle variable unit, monitors a detected intensity by the detection element that detects an intensity of the nearly parallel X-ray beam reflected by the sample, and adjusts to, as the half intensity height, a height of the sample surface in a state in which the detected intensity being monitored becomes half of the start intensity of half intensity adjustment and the detected intensity being monitored decreases if an irradiation angle of the nearly parallel X-ray beam is increased/decreased by the irradiation angle variable unit.

6. The X-ray reflectometer as claimed in claim 4, wherein the slit to form the focused X-ray beam is a variable slit configured to further limit the focusing angle width to form a nearly parallel X-ray beam,
the X-ray reflectometer further comprises a half intensity height adjustment unit configured to adjust the height of the sample surface to a half intensity height by the sample height setting unit, and
the half intensity height adjustment unit, on the basis of a half intensity adjustment method,
    in a state in which the sample is retracted by the sample height setting unit, causes the nearly parallel X-ray beam formed by the variable slit to be emitted toward the position sensitive detector, and stores, as a start intensity of half intensity adjustment, a detected intensity by the detection element that detects an intensity of the nearly parallel X-ray beam, and while operating the sample height setting unit and the irradiation angle variable unit, monitors a detected intensity by the detection element that detects an intensity of the nearly parallel X-ray beam reflected by the sample, and adjusts to, as the half intensity height, a height of the sample surface in a state in which the detected intensity being monitored becomes half of the start intensity of half intensity adjustment and the detected intensity being monitored decreases if an irradiation angle of the nearly parallel X-ray beam is increased/decreased by the irradiation angle variable unit.

7. The X-ray reflectometer as claimed in claim 5, further comprising a position sensor configured to detect the height of the sample surface, wherein
the half intensity height adjustment unit stores a half intensity height adjusted for a predetermined sample, by detecting the half intensity height using the position sensor, and adjusts, for a given sample, a height of a sample surface thereof to the stored half intensity height by the sample height setting unit.

8. The X-ray reflectometer as claimed in claim 6, further comprising a position sensor configured to detect the height of the sample surface, wherein
the half intensity height adjustment unit stores a half intensity height adjusted for a predetermined sample, by detecting the half intensity height using the position sensor, and adjusts, for a given sample, a height of a sample surface thereof to the stored half intensity height by the sample height setting unit.

9. The X-ray reflectometer as claimed in claim 5, further comprising a reflection angle correcting unit configured to correct a reflection angle associated with a position in the height direction of each detection element, wherein
the reflection angle correcting unit
has stored, as an origin height position, a position in the height direction of the detection element that detects an intensity of the nearly parallel X-ray beam when the nearly parallel X-ray beam formed by the variable slit is emitted toward the position sensitive detector in a state in which the irradiation angle by the irradiation angle variable unit is set at 0 degrees and the sample is retracted by the sample height setting unit,
stores, as a set angle corresponding height position, a position in the height direction of the detection element that detects an intensity of the nearly parallel X-ray beam formed by the variable slit and reflected by the sample, in a state in which the irradiation angle by the irradiation angle variable unit is a set angle smaller than a total reflection critical angle, and under the adjustment of the half intensity height by the half intensity height adjustment unit, and
for the integration of the detected intensity by the corresponding detection element per reflection angle by the reflection intensity calculation unit, calculates the corrected reflection angle by triangulation on the basis of the origin height position, the receiving distance, the set angle, and the set angle corresponding height position.

10. The X-ray reflectometer as claimed in claim 6, further comprising a reflection angle correcting unit configured to correct a reflection angle associated with a position in the height direction of each detection element, wherein
the reflection angle correcting unit
has stored, as an origin height position, a position in the height direction of the detection element that detects an intensity of the nearly parallel X-ray beam when the nearly parallel X-ray beam formed by the variable slit is emitted toward the position sensitive detector in a state in which the irradiation angle by the irradiation angle variable unit is set at 0 degrees and the sample is retracted by the sample height setting unit,
stores, as a set angle corresponding height position, a position in the height direction of the detection element that detects an intensity of the nearly parallel X-ray beam formed by the variable slit and reflected by the sample, in a state in which the irradiation angle by the irradiation angle variable unit is a set angle smaller than a total reflection critical angle, and under the adjustment of the half intensity height by the half intensity height adjustment unit, and
for the integration of the detected intensity by the corresponding detection element per reflection angle by the reflection intensity calculation unit, calculates the corrected reflection angle by triangulation on the basis of the origin height position, the receiving distance, the set angle, and the set angle corresponding height position.

11. The X-ray reflectometer as claimed in claim 1, wherein
the position sensitive detector includes an attenuator configured to attenuate the intensity of the reflected X-ray beam at a part of a receiving surface thereof.

12. The X-ray reflectometer as claimed in claim 1, wherein
the focused X-ray beam formation unit further has a knife edge slit located close to an irradiation position of the focused X-ray beam on the sample surface.

13. The X-ray reflectometer as claimed in claim 1, wherein
when, for only the detection elements positioned within the divergence angle width of the reflected X-ray beam in the position sensitive detector, per reflection angle of the reflected X-rays constituting the reflected X-ray beam, integrating the detected intensity by the corresponding detection element, the reflection intensity calculation unit calculates a background intensity on the basis of the detected intensities by the detection elements positioned outside the divergence angle width of the reflected X-ray beam in the position sensitive detector, and subtracts the background intensity.

* * * * *